United States Patent
Weibel et al.

(10) Patent No.: US 11,191,895 B2
(45) Date of Patent: Dec. 7, 2021

(54) DEVICE AND SYSTEM FOR DISPENSING A FLUID UNDER ASEPTIC CONDITIONS

(71) Applicant: WEIBEL CDS AG, Waldstatt (CH)

(72) Inventors: Ludwig Daniel Weibel, Waldstatt (CH); Samuel Wyler, Abtwil (CH)

(73) Assignee: SHL MEDICAL AG, Zug (CH)

(*) Notice: Subject to any disclaimer, the term of this patent is extended or adjusted under 35 U.S.C. 154(b) by 273 days.

(21) Appl. No.: 16/305,208

(22) PCT Filed: May 17, 2017

(86) PCT No.: PCT/EP2017/061883
§ 371 (c)(1),
(2) Date: Nov. 28, 2018

(87) PCT Pub. No.: WO2017/211558
PCT Pub. Date: Dec. 14, 2017

(65) Prior Publication Data
US 2019/0201618 A1    Jul. 4, 2019

(30) Foreign Application Priority Data
Jun. 8, 2016 (EP) .................... 16173551

(51) Int. Cl.
*A61M 5/162* (2006.01)
*A61M 5/142* (2006.01)
(Continued)

(52) U.S. Cl.
CPC .......... *A61M 5/162* (2013.01); *A61M 5/1456* (2013.01); *A61M 5/14244* (2013.01);
(Continued)

(58) Field of Classification Search
CPC ................ A61M 5/162; A61M 5/1456; A61M 5/14244; A61M 5/31511; A61M 39/165; A61M 2005/14268; A61M 5/14212
See application file for complete search history.

(56) References Cited

U.S. PATENT DOCUMENTS

2002/0087144 A1* 7/2002 Zinger ................ A61M 39/223
604/523
2002/0123719 A1* 9/2002 Lavi ..................... A61J 1/2089
604/82

(Continued)

FOREIGN PATENT DOCUMENTS

| WO | 2008/024814 A2 | 2/2008 |
| WO | 2014/051257 A1 | 1/2014 |
| WO | 2014/191038 A1 | 12/2014 |

OTHER PUBLICATIONS

"Definition of Cam," Merriam-Webster Online Dictionary, <https://www.merriam-webster.com/dictionary/cam>. (Year: 2021).*

(Continued)

*Primary Examiner* — Nathan R Price
*Assistant Examiner* — Tasnim Mehjabin Ahmed
(74) *Attorney, Agent, or Firm* — McDonnell Boehnen Hulbert & Berghoff LLP

(57) ABSTRACT

A device (1) for dispensing a fluid, in particular under aseptic conditions, preferably to a patient. The device comprises a conveying device (2) for conveying the fluid to a dispensing opening (3). The device (1) also comprises a coupling element (4) for coupling a syringe (5). The fluid can be conveyed from the syringe (5) to the dispensing opening (3) via the coupling element (4) and the conveying device (2) exclusively by the effect of the conveying device (2). The invention further relates to a system for dispensing (Continued)

a fluid under aseptic conditions, comprising such a device (1) and to a syringe (5) that can be coupled to the coupling element (4).

11 Claims, 3 Drawing Sheets

(51) Int. Cl.
    *A61M 5/315*     (2006.01)
    *A61M 39/16*     (2006.01)
    *A61M 5/145*     (2006.01)
    *A61M 39/00*     (2006.01)

(52) U.S. Cl.
    CPC ...... *A61M 5/31511* (2013.01); *A61M 39/165* (2013.01); *A61M 2005/14268* (2013.01); *A61M 2039/0036* (2013.01); *A61M 2205/12* (2013.01)

(56) References Cited

U.S. PATENT DOCUMENTS

| | | | |
|---|---|---|---|
| 2008/0077081 A1* | 3/2008 | Mounce | A61M 5/1413 604/67 |
| 2010/0174266 A1 | 7/2010 | Estes | |
| 2014/0025008 A1* | 1/2014 | Sims | A61M 5/14244 604/151 |
| 2016/0121043 A1 | 5/2016 | Weibel | |

OTHER PUBLICATIONS

International Search Report Corresponding to PCT/EP2017/061883 dated Aug. 14, 2017.
Written Opinion Corresponding to PCT/EP2017/061883 dated Aug. 14, 2017.

* cited by examiner

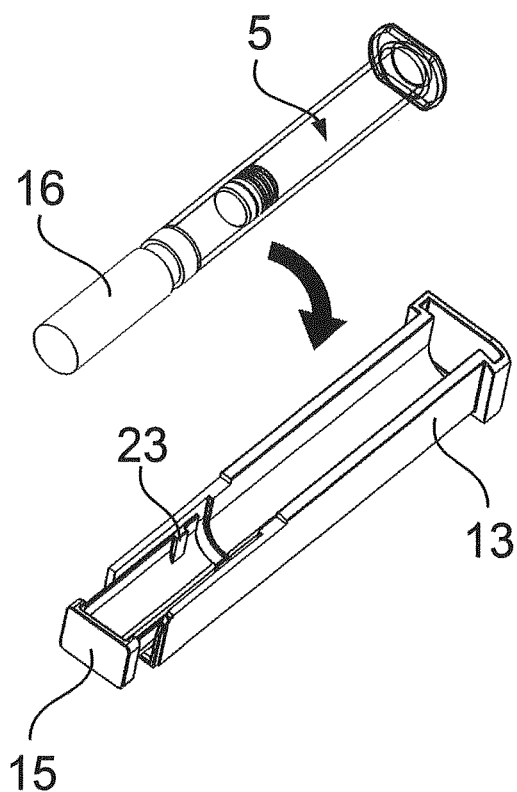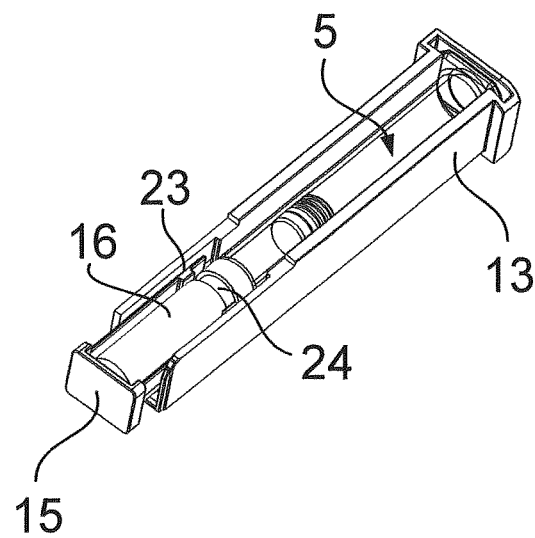
Fig. 4  Fig. 5
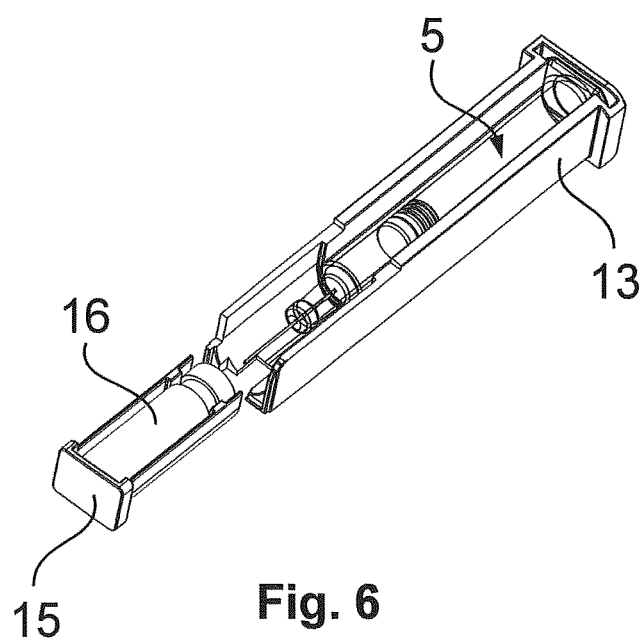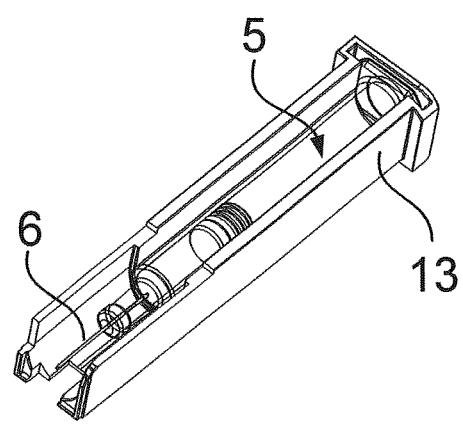
Fig. 6  Fig. 7

DEVICE AND SYSTEM FOR DISPENSING A FLUID UNDER ASEPTIC CONDITIONS

The present invention relates to a device and a system for dispensing a fluid, in particular under aseptic conditions, preferably to a patient, and to the use of such a device or of such a system for dispensing a fluid, in particular under aseptic conditions, preferably to a patient, in accordance with the preambles of the independent claims.

For the parenteral injection of liquid formulations of pharmaceutical substances, drug pumps have in recent times also proven useful besides injection syringes and drug pens. Such pumps are advantageous in particular when a preparation has to be administered to a patient in accordance with a precisely defined program, for example over quite a long period of time, independently of the presence of medical personnel. Depending on their intended use, the pumps can be placed onto the body of the patient and typically comprise a container for the liquid formulation, and also a delivery device which delivers this formulation to a port or to an injection system. The injection system can comprise an indwelling cannula, which remains in the patient's body over the entire period of the administration.

The drug Neulasta® contains the active substance pegfilgrastim, which belongs to the group called cytokines and is very similar to an endogenous protein, the granulocyte colony-stimulating factor. Neulasta® is used to shorten the duration of neutropenia (low white blood cell count) and to reduce the occurrence of febrile neutropenia (low white blood cell count with fever). These conditions may be caused by the use of cytotoxic chemotherapy (drugs that destroy rapidly growing cells). If the white blood cell count drops to a low level, this may mean that the body no longer has enough of these cells to fight pathogens, which leads to an increased risk of infection.

Neulasta® is available as a prefilled syringe containing an individual dose of 6 mg in 0.6 ml of injection solution. The solution is injected subcutaneously (i.e. under the skin). It has to be administered according to a strict timetable, normally 24 hours after the last dose of chemotherapy at the end of each treatment cycle. If it is not administered as instructed, the product may in some cases have no effect.

To make administration of Neulasta® easier for the patient, the drug, supplied in a disposable syringe, is offered as a kit with a drug pump (tradename Onpro™). The solution from the syringe has to be introduced through an opening into the drug pump by trained medical personnel. Once placed on the body of the patient, the drug is dispensed 27 hours after activation of the pump, for a period of 45 minutes. Using the drug pump has the advantage that a new visit to the physician, simply for the administration of Neulasta®, is no longer necessary. Moreover, since the patient does not have to self-inject the product, this prevents him from forgetting the dose or from making mistakes that specifically affect his state of health.

However, the Onpro™ drug pump has a relatively large number of individual parts, for which reason it is complicated and expensive to manufacture. In addition, the solution in the prefilled syringe has to be introduced into the drug pump through a comparatively small septum. This can only be done by medical personnel. There is also the danger of contaminating the solution during the transfer procedure.

It is therefore an object of the present invention to overcome the disadvantages of the prior art. In particular, it is an object of the invention to make available a versatile and structurally simple device for dispensing a fluid under aseptic conditions, preferably to a patient, which device is more cost-effective to produce. Moreover, the device is intended to be suitable for handling by the patient.

These objects are achieved by a device and a system that have the features of the independent claims.

The device for dispensing a fluid, in particular under aseptic conditions, preferably to a patient, comprises a delivery device for delivering the fluid to a dispensing opening. The device further comprises a coupling element for coupling a syringe. The fluid can be delivered from the syringe to the dispensing opening via the coupling element and the delivery device exclusively by the effect of the delivery device.

In particular, the delivery device generates an underpressure at the syringe, as a result of which the content of the syringe is suctioned from the latter and, under the effect of the suction force, the plunger of the syringe moves in the direction of the proximal end of the syringe. It goes without saying that the delivery device for this purpose has to provide a sufficient suction force.

This configuration of the device means that it is possible to do without a separate container for receiving the fluid. This function is taken over by the syringe, which is in many cases prefilled with the fluid by the manufacturer. In this way, the total number of parts of the system can be reduced, which results in greater reliability and lower costs. Since pharmaceuticals are subject to stringent regulations and the launch of new packaging has to be registered, it is moreover advantageous that a traditional syringe can be used both for the injection and also in connection with the device. It is thus possible to avoid further complex and costly approval procedures. Since the fluid does not have to be transferred into a further container and is instead transferred directly from the syringe to the patient via the delivery device, it is additionally possible to reduce the risk of contaminating the fluid and thus placing the patient in danger.

A further aspect of the present invention relates to a device which has the abovementioned features but which generally comprises a coupling element for coupling a cylindrical container with a stopper that is displaceable in a longitudinal direction. The fluid can then be delivered from the container to the dispensing opening via the coupling element and the delivery device exclusively by the effect of the delivery device. Besides being a syringe, a container of this kind can be in the form of a carpule, for example.

The coupling element can comprise a septum that is pierceable by a syringe needle or cannula. This is particularly advantageous if the syringe comprises a fixedly mounted syringe needle or cannula, as is generally customary in prefilled syringes. However, this configuration is also advantageous in syringes with an exchangeable needle, since the connection between the syringe and the delivery device can thus be produced in an extremely hygienic way.

The coupling element can be configured as a needle receiver into which the septum is fitted, in particular into a peripheral groove. The needle receiver can be configured as a conduit section, in particular a curved conduit section. The configuration of the coupling element as a needle receiver has the advantage that the needle can be guided in a controlled manner, for piercing the septum, and can thereafter be held secure. The needle receiver can be formed in one piece with the housing of the device. This means that a device of this kind with a needle receiver can be of simple construction and can be produced in an efficient and cost-effective manner.

The needle receiver can be in fluidic communication with a conduit element, in particular a steel cannula, wherein the conduit element is preferably embedded, in particular overmoulded, in a wall of the needle receiver or is connected to the needle receiver via a sealing element, in particular a further septum, which is preferably fitted into a peripheral groove of the needle receiver. By way of the conduit element, the needle receiver can be fluidically connected to further parts of the device, in particular to the delivery device. The embedding of the conduit element in a wall of the needle receiver or the use of a sealing element are advantageous design variants for connecting the conduit element to the needle receiver.

The device can comprise a holder into which the syringe or the carpule is insertable, wherein the syringe or the carpule, when inserted into the holder, can be coupled to the device via the coupling element. A holder has the advantage that the syringe or the carpule, when connected to the device, is held securely at its intended position. Moreover, the coupling of the syringe or the carpule to the coupling element can be simplified, in particular guided, by the holder. In this way, a device of this kind can also be safely used by persons who are not medically trained, in particular by the actual patient.

The holder can be configured as a drawer unit which can be pushed into a drawer region of the device. The use of the device may be further simplified by the syringe or the carpule being inserted into a drawer unit before the latter is pushed into the device and before the device is thus coupled to the coupling element. The drawer unit can have a pull-off element, with which a protective cap of a syringe or carpule inserted into the drawer unit can be pulled off. This may further simplify the use of the device, in particular by a patient.

A further aspect of the present invention relates to a system for dispensing a fluid, in particular under aseptic conditions, preferably to a patient, said system comprising a device as described above and a syringe or carpule that can be coupled to the coupling element. By making the device and the syringe or carpule available as a system, a syringe or carpule can be supplied that is specifically adapted to this device. This applies in particular to the dimensions of the syringe or carpule, for example to the length and the diameter of a fixedly mounted syringe needle, and to the general configuration thereof. For example, it is possible that the syringe is configured without a plunger rod. This in particular reduces the overall length of the syringe when the plunger is pulled back, which is advantageous especially in prefilled syringes in order to reduce the size of the device and of the syringe packaging.

The syringe can be a hollow needle or cannula that is mounted in particular fixedly on the syringe body. This is nowadays customary in prefilled syringes. On the one hand, this can avoid contamination of the fluid during fitting of a separate syringe needle. On the other hand, this makes use easier, since it avoids a separate step for fitting a syringe needle or cannula.

In a system of this kind, the device can comprise a syringe holder which is configured in such a way that the syringe needle or cannula of a syringe inserted therein can be shielded. This can largely avoid a situation where a person using the device injures himself on the syringe needle after removal of the protective cap.

The present invention further relates to the use of a device or of a system as described above for dispensing a fluid, in particular under aseptic conditions.

Further advantages and individual features of the invention will become clear from the following description of an illustrative embodiment and from the schematic drawings, in which:

FIGS. 4 to 7 show perspective views of a sequence of steps involving the insertion of a syringe into the drawer unit of a device according to FIGS. 1 to 3 and the pulling-off of the protective cap of the syringe.

Figure 1:
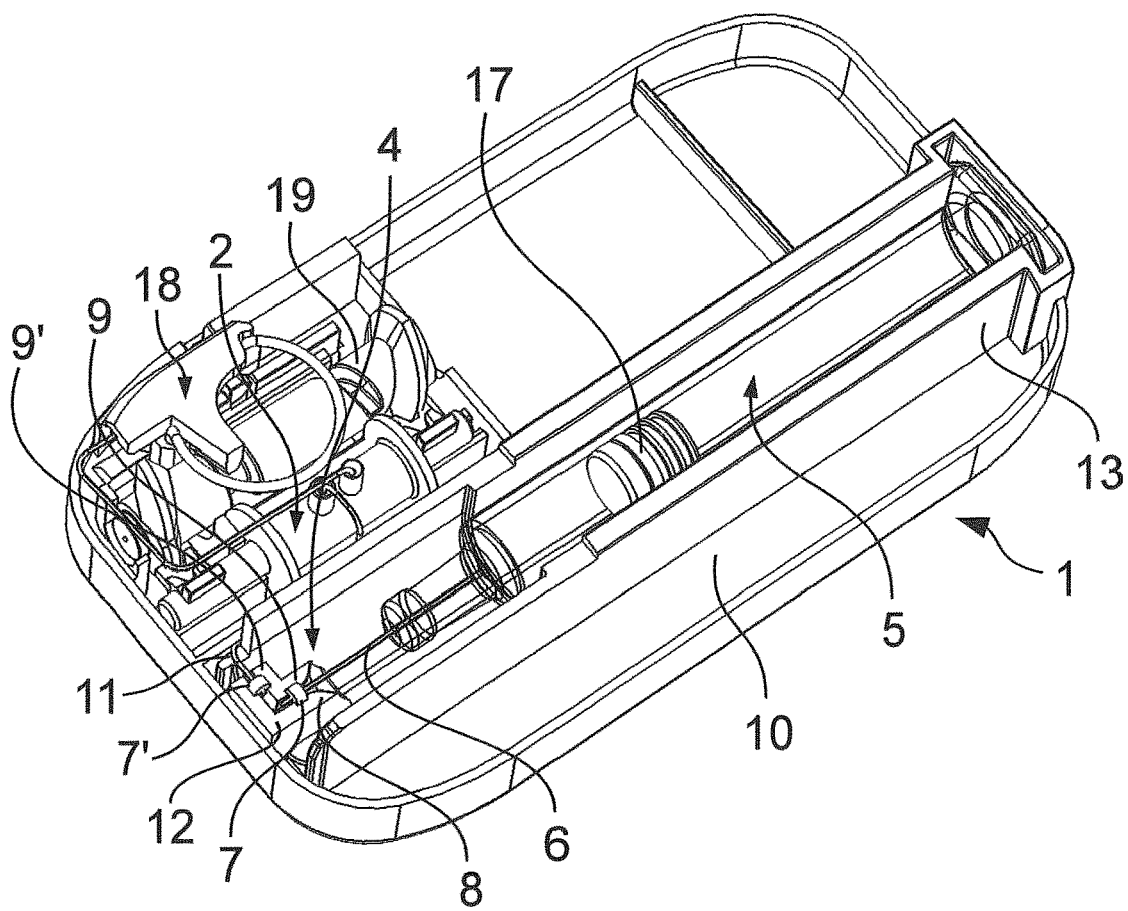
FIG. 1 shows a perspective view of the top of a device according to the invention.

FIG. 1 shows a device 1 according to the invention, wherein the upper part of a housing 10 has been omitted in order to provide greater clarity. Moreover, individual parts of the device 1, for example a delivery drive or control electronics, are not shown. In the device shown, a holder for the syringe 5 is configured as a drawer unit 13, which is here pushed into the device 1. The syringe 5 has a plunger 17 on which, in contrast to customary syringes, no plunger rod is mounted. Moreover, the syringe 5 has a fixedly mounted syringe needle 6. It will be seen that the syringe needle 6 protrudes into a coupling element 4 which, in the present example, is configured as a needle receiver 8. The region of the needle receiver 8 directed toward the syringe 5 has a funnel-shaped configuration in order to guide the syringe needle 6 in the direction of a septum 7. The septum 7 is embedded in a peripheral groove 9 of a wall 12 of the needle receiver 8. The needle receiver 8 is configured as a curved conduit section which is formed in one piece with the housing 10 of the device 1. The needle receiver 8 is connected to the delivery device 2 via a conduit element 11, which is here configured as a steel cannula. The fluidic attachment of the conduit element 11 to the needle receiver 8 is via a septum 7', which is likewise embedded in a peripheral groove 9' inside the wall 12 of the needle receiver 8. Besides the delivery device 2, the device 1 has an injection device 18, and these are both actuated or controlled via a barrel cam 19 driven by a delivery drive (not shown).

Figure 2:
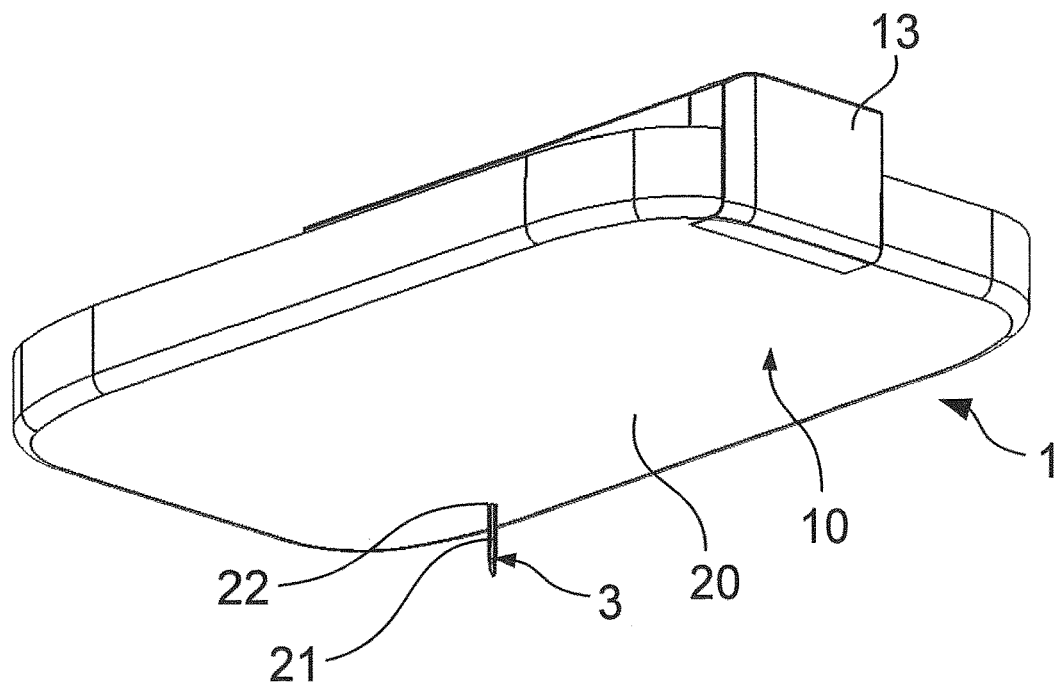
FIG. 2 shows a perspective view of the underside of the device according to FIG. 1.

FIG. 2 shows an underside of the device 1. It will be seen that the housing 10 there has a contact face 20 via which the device 1 is to be placed onto the body of a patient, in particular via an adhesive film. In the illustrative embodiment of the device 1 shown, a dispensing opening 3 is configured as a combination of puncture cannula and indwelling cannula 21, which are applied through the opening 22 in the housing 10 via an applicator mechanism of the injection device 8.

Figure 3:
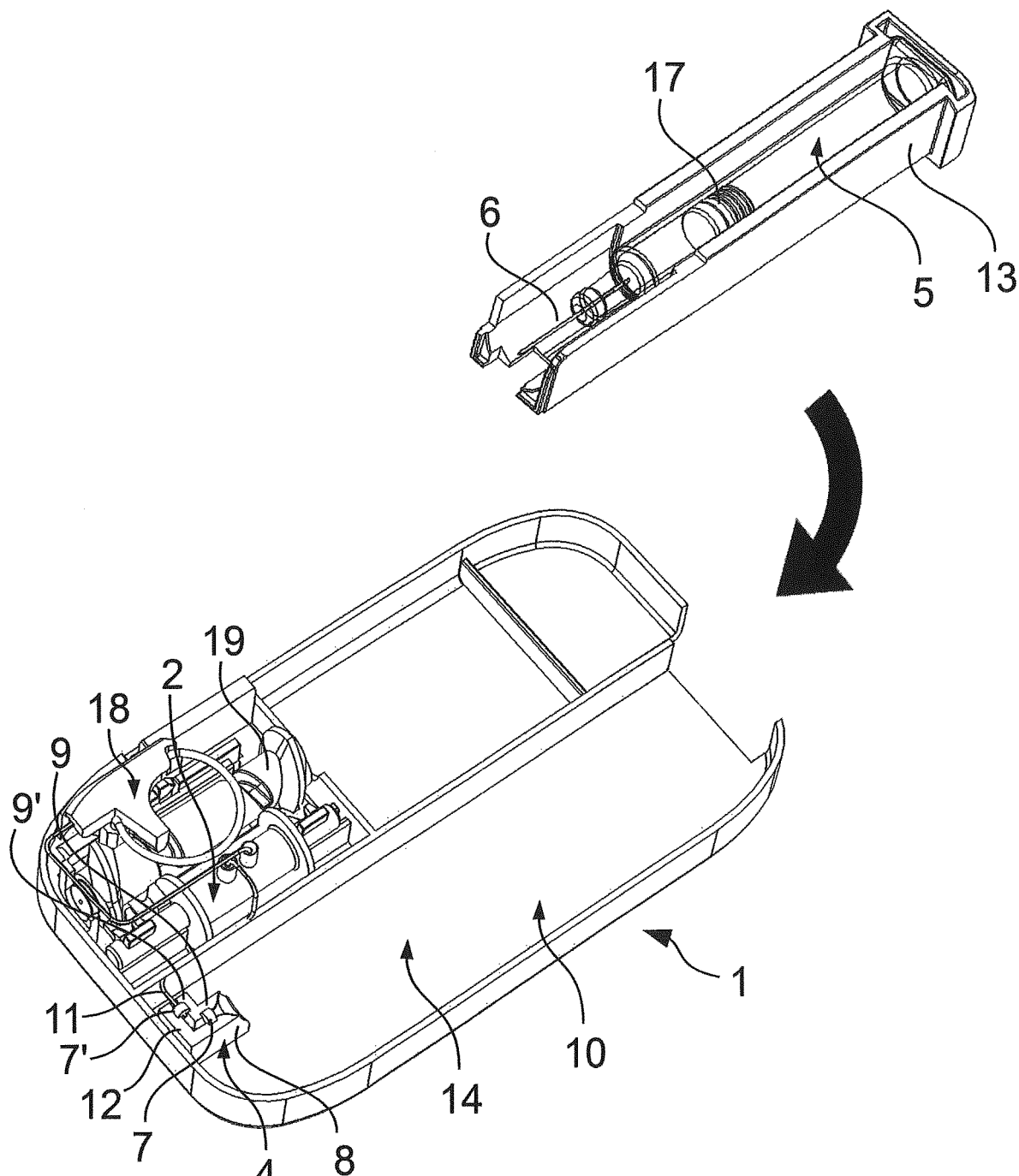
FIG. 3 shows a perspective view of the device according to FIGS. 1 and 2, but with the holder shown separately and configured as a drawer unit into which a syringe in inserted.

In FIG. 3, the device 1 described above and the drawer unit 13 with the syringe 5 are shown separately. It will be seen that the syringe needle 6 is largely shielded by the drawer unit 13, thus making it possible to prevent a user from injuring himself on the needle. The drawer unit 13 is pushed into a drawer region 14 of the device 1, as a result of which the syringe needle 6 is guided into the needle receiver 8 and the septum 7 is pierced.

FIGS. 4 to 7 show the insertion of the syringe 5 into the drawer unit 13 and the pulling-off of a protective cap 16 from the syringe 5. In FIG. 4, the drawer unit 13 with a pull-off element 15, on the one hand, and the syringe 5 with the protective cap 16, on the other hand, are shown individually. In FIG. 5, the syringe 5 is inserted into the drawer unit 13. It will be seen that engagement elements 23 of the pull-off element 15 engage in a groove 24 of the protective cap 16. In FIG. 6, the protective cap 16 has already been pulled off with the pull-off element 15 from the syringe 5. FIG. 7 shows the drawer unit 13 with the inserted syringe 5 ready to be pushed into the device 1. It will be seen that the syringe needle 6 of the syringe 5 is substantially shielded by the drawer unit 13, thus making it possible to prevent a user from injuring himself on the syringe needle 6.

The invention claimed is:

1. A device for dispensing a fluid, comprising:
   a housing;
   a holder removably and slidably positioned inside of the housing and comprising an open proximal end;
   a container of fluid positioned in the holder, where the container does not have a plunger rod and has a distal end, a proximal end and comprises a slidable plunger that seals the distal end, where the plunger moves axially towards the proximal end as the fluid is dispensed through a needle cannula connected to the proximal end and extends into the open proximal end of the holder; and
   a delivery device that creates a suction force on the fluid within the container during fluid dispensing for delivering the fluid to a dispensing opening, wherein the device for dispensing a fluid further comprises a coupling element that extends into the open proximal end of the holder to form a fluid communication with the needle cannula and the delivery device, where the coupling element comprises a septum that is pierced by the needle cannula,
   wherein the fluid communication is formed when the holder containing the container of fluid is inserted into the housing causing the needle cannula to pierce the septum.

2. The device according to claim 1, wherein the coupling element further comprises a needle receiver into which the septum is fitted.

3. The device according to claim 2, wherein the needle receiver has a conduit section.

4. The device according to claim 2, wherein the needle receiver is formed as an integral part of the housing of the device for dispensing a fluid.

5. The device according to claim 2, wherein the needle receiver is in fluidic communication with a conduit element, and the conduit element is embedded in a wall of the needle receiver or is connected to the needle receiver via a sealing element.

6. The device according to claim 1, wherein the housing comprises a drawer region and the holder is designed in the shape of a drawer that is pushed into the drawer region of the device for dispensing a fluid prior to dispensing of the fluid.

7. The device according to claim 6, further comprising a protective cap removably attached to the proximal end of the container and covering the needle cannula, wherein the drawer comprises a removable pull-off element having an attachment element that engages the protective cap on the container when the pull-off element is moved axially relative to the drawer.

8. A system for dispensing a fluid under aseptic conditions, said system comprising the device for dispensing a fluid according to claim 1, where the holder is configured as a drawer detached from the housing, where the drawer is configured to accept and hold the container and to slide into the housing such that the needle cannula is coupled to the coupling element.

9. The system according to claim 8, wherein the container comprises a syringe having a syringe body, where the needle cannula is mounted on the syringe body.

10. The system according to claim 9, further comprising a protective cap removably attached to the syringe covering the needle cannula when the syringe is positioned in the drawer.

11. The system according to claim 10, wherein the drawer comprises a removable pull-off element having an attachment element that engages the protective cap when the pull-off element is moved axially relative to the drawer.

* * * * *